US006335190B1

(12) United States Patent
Zhou et al.

(10) Patent No.: US 6,335,190 B1
(45) Date of Patent: Jan. 1, 2002

(54) METHOD FOR CLONING AND PRODUCING THE BSMI RESTRICTION ENDONUCLEASE IN *E. COLI*

(75) Inventors: Jing Zhou; Zhenyu Zhu, both of Beverly; Shuang-yong Xu, Lexington, all of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/693,147

(22) Filed: Oct. 20, 2000

(51) Int. Cl.⁷ .............................................. C12N 15/55
(52) U.S. Cl. ................. 435/199; 435/320.1; 435/252.3; 536/23.2
(58) Field of Search .............................. 435/199, 320.1, 435/252.3; 536/23.2

(56) References Cited

U.S. PATENT DOCUMENTS

| 5,200,333 A | 4/1993 | Wilson ..................... 435/172.3 |
| 5,498,535 A | 3/1996 | Fomenkov et al. ....... 435/172.3 |

OTHER PUBLICATIONS

Roberts and Macelis, Nucleic Acids Res. 27:312–313 (1999).
Kosykh, et al., Mol. Gen. Genet. 178:717–719 (1980).
Mann, et al., Gene, 3:97–112 (1978).
Walder, et al., Proc. Natl. Acad. Sci. 78:1503–1507 (1981).
Bougueleret, et al., Nucleic Acids Res. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriology 164:501–509 (1985).
Wayne, et al., Gene 202:83–88 (1997).
Kiss, et al., Nucleic Acids Res. 13:6403–6421 (1985).
Szomolanyi, et al., Gene 10:219–225 (1980).
Janulaitis, et al., Gene 20:197–204 (1982).
Kiss and Baldauf, Gene 21:111–119 (1983).
Walder, et al., J. Biol. Chem. 258:1235–1241 (1983).
Fomenkov, et al., Nucleic Acids Res. 22:2399–2403 (1994).

*Primary Examiner*—Charles L. Patterson, Jr.
(74) *Attorney, Agent, or Firm*—Gregory D. Williams

(57) ABSTRACT

The present invention relates to recombinant DNA which encodes the BsmI restriction endonuclease as well as BsmI methyltransferases, expression of BsmI restriction endonuclease in *E. coil* cells containing the recombinant DNA by using a low copy number T7 expression vector pACYC-T7ter, and purification of BsmI restriction endonuclease by heat treatment and chromatography through heparin Sepharose column.

6 Claims, 6 Drawing Sheets

GENE ORGANIZATION OF BsmI R-M SYSTEM

RECOGNITION SEQUENCE: 5' GAATGCN^ 3'
                     3' CTTAC^GN 5'

(ParA)   bsmIM1   ORF   bsmIM2   bsmIR

FIG. 2

```
     ATGCTTTCAGAATGGATTAATACCATCCAAAATACAGAATGTATACAATCAATGAAAAAA
  1  ------------+----------+----------+----------+----------+----------+  60
      M  L  S  E  W  I  N  T  I  Q  N  T  E  C  I  Q  S  M  K  K
     TTACCGGATAACTCAATTGACTTAGTAATTGCTGATCCCCCATATAATTTGTCAAAAGGA
 61  ------------+----------+----------+----------+----------+----------+ 120
      L  P  D  N  S  I  D  L  V  I  A  D  P  P  Y  N  L  S  K  G
     GGTAAATGGAAATGGGATAATAGTAAAAAGTTGGTTGGTATGGGTGGTAATTGGAATAAA
121  ------------+----------+----------+----------+----------+----------+ 180
      G  K  W  K  W  D  N  S  K  K  L  V  G  M  G  G  N  W  N  K
     GTAATGGAAAATTGGGATGATATGACATTCGAAGAGTATTGGGAATTCACGGAGTCTTGG
181  ------------+----------+----------+----------+----------+----------+ 240
      V  M  E  N  W  D  D  M  T  F  E  E  Y  W  E  F  T  E  S  W
     CTATTGGAGGTAAAGCGTATTTTAAAACCAACGGGTTCTCTATGGATATTTGGTACTTAT
241  ------------+----------+----------+----------+----------+----------+ 300
      L  L  E  V  K  R  I  L  K  P  T  G  S  L  W  I  F  G  T  Y
     CATAATATGGGAATAATAAATGTCGTTTGTCAGAAGCTTGGAATAGAAATTATAAATGAG
301  ------------+----------+----------+----------+----------+----------+ 360
      H  N  M  G  I  I  N  V  V  C  Q  K  L  G  I  E  I  I  N  E
     ATTATATGGTATAAGAGAAATGCATTTCCAAATTTATCGGGTCGTAGATTCACTGCTAGT
361  ------------+----------+----------+----------+----------+----------+ 420
      I  I  W  Y  K  R  N  A  F  P  N  L  S  G  R  R  F  T  A  S
     CATGAAACAATTCTTTGGTGTCATGTTGGCCAGAAAAAAAGGGAATATTATTTTAACTAT
421  ------------+----------+----------+----------+----------+----------+ 480
      H  E  T  I  L  W  C  H  V  G  Q  K  K  R  E  Y  Y  F  N  Y
     GAGTATGTGAAAAATGCTTCTTTCCCTGAGGATATGCTAAAATCCCCTGGAAAACAAATG
481  ------------+----------+----------+----------+----------+----------+ 540
      E  Y  V  K  N  A  S  F  P  E  D  M  L  K  S  P  G  K  Q  M
     AGAACTGTTTGGGATATCCCTAATAACAAACAAAAAGACGAGTTAAAGTTTGGAAAACAT
541  ------------+----------+----------+----------+----------+----------+ 600
      R  T  V  W  D  I  P  N  N  K  Q  K  D  E  L  K  F  G  K  H
     CCAACTCAAAAACCTCTTAGATTACTTCATAGAATAATATTAGCAACAAGTAAAGAGGGC
601  ------------+----------+----------+----------+----------+----------+ 660
      P  T  Q  K  P  L  R  L  L  H  R  I  I  L  A  T  S  K  E  G
     GATATTTGTCTGGCACCGTTTAGTGGAGTTGGTAGTGAATGCGTTGCGGCTAAGGAACTA
661  ------------+----------+----------+----------+----------+----------+ 720
      D  I  C  L  A  P  F  S  G  V  G  S  E  C  V  A  A  K  E  L
     GGGCGGAATTTTATAGGTTTTGAAATTAACAAGGAATATTACGATATTTCTCTTAAACGT
721  ------------+----------+----------+----------+----------+----------+ 780
      G  R  N  F  I  G  F  E  I  N  K  E  Y  Y  D  I  S  L  K  R
     ATAGAATCTACTCAGAAAAAAATTGAGCAAATTTGTATGAATTTATAA
781  ------------+----------+----------+----------+------   828
      I  E  S  T  Q  K  K  I  E  Q  I  C  M  N  L  *
```

FIG. 3

```
      ATGAACAAAATCTCTTTTCAACCTGCTATAAAATGGAGTGGCAGTAAAAGAAGCCAAGCA
  1   ----------+---------+---------+---------+---------+---------+   60
      M  N  K  I  S  F  Q  P  A  I  K  W  S  G  S  K  R  S  Q  A
      TGGAATATAATAAAATTGTTTCCTAAATTTGATCGATATTATGAACCGTTTGTTGGGGGG
 61   ----------+---------+---------+---------+---------+---------+  120
      W  N  I  I  K  L  F  P  K  F  D  R  Y  Y  E  P  F  V  G  G
      GCATCCATAACATATGCTTTAAACCCAAATAGAGGTATATGCGGTGATATATGCAAACCA
121   ----------+---------+---------+---------+---------+---------+  180
      A  S  I  T  Y  A  L  N  P  N  R  G  I  C  G  D  I  C  K  P
      CTAATTGAAATTTGGAAAATTATCAAAAGTGATCCTCTAAGTATTGTAAATGAGTATAAA
181   ----------+---------+---------+---------+---------+---------+  240
      L  I  E  I  W  K  I  I  K  S  D  P  L  S  I  V  N  E  Y  K
      AAAAGATGGATACTACTTCAAGAGCAAGGACATACTGTATATTACGAAATTCGCGACAAT
241   ----------+---------+---------+---------+---------+---------+  300
      K  R  W  I  L  L  Q  E  Q  G  H  T  V  Y  Y  E  I  R  D  N
      TTTAACAAAACTCAAAATCCGTATGACTTATTTTTCCTCACAAGAACTTGTGTAAATGGG
301   ----------+---------+---------+---------+---------+---------+  360
      F  N  K  T  Q  N  P  Y  D  L  F  F  L  T  R  T  C  V  N  G
      CTTATAAGATTTAATAAAGATGGTTTATTCAACAATTCATTCCATCATACAAGAAAAGGG
361   ----------+---------+---------+---------+---------+---------+  420
      L  I  R  F  N  K  D  G  L  F  N  N  S  F  H  H  T  R  K  G
      ATACACCCTGATAAGTTACATAAAATTATCTTGAATTGGTCATATAGATTAAAGAATATA
421   ----------+---------+---------+---------+---------+---------+  480
      I  H  P  D  K  L  H  K  I  I  L  N  W  S  Y  R  L  K  N  I
      GAATTTAGGCACGGCGATTATAGAGTAACAACTGAAGATATAACAAAAAATGACTTTATT
481   ----------+---------+---------+---------+---------+---------+  540
      E  F  R  H  G  D  Y  R  V  T  T  E  D  I  T  K  N  D  F  I
      TATCTAGATCCTCCGTACTTTAATACGCGTGGAAGATACTATGGGACAATTGATTTTAAT
541   ----------+---------+---------+---------+---------+---------+  600
      Y  L  D  P  P  Y  F  N  T  R  G  R  Y  Y  G  T  I  D  F  N
      GAATTCCTTGAATTTCTTTATTCGCTAAACTCCAGAGGAATAAAATTTGCTTTATCTTTC
601   ----------+---------+---------+---------+---------+---------+  660
      E  F  L  E  F  L  Y  S  L  N  S  R  G  I  K  F  A  L  S  F
      GATGGTAAACGAGAAGATGTAAATTACATGGTTGAATTACCAAAGGATTTGTATAAAAGA
661   ----------+---------+---------+---------+---------+---------+  720
      D  G  K  R  E  D  V  N  Y  M  V  E  L  P  K  D  L  Y  K  R
      CATATATTAATAGAAtCCGGTAACTCAAGTTTCAAAAAGGTAATGGATAAAGATCCTCAA
721   ----------+---------+---------+---------+---------+---------+  780
      H  I  L  I  E  S  G  N  S  S  F  K  K  V  M  D  K  D  P  Q
      AAAGTCTTCGAATCCTTATATCTTAATTGGTGA
781   ----------+---------+----  813
      K  V  F  E  S  L  Y  L  N  W  *
```

FIG. 4A

```
    ATGAATGTTTTTAGAATTCATGGTGATAATATTATTGAGTGTGAGAGAGTTATAGATTTG
1   ------------+---------+---------+---------+---------+---------+  60
     M  N  V  F  R  I  H  G  D  N  I  I  E  C  E  R  V  I  D  L
    ATATTATCAAAAATCAATCCCCAGAAAGTAAAAAGAGGGTTTATTTCATTATCATGCCCT
61  ------------+---------+---------+---------+---------+---------+  120
     I  L  S  K  I  N  P  Q  K  V  K  R  G  F  I  S  L  S  C  P
    TTTATAGAAATTATATTCAAAGAGGGTCATGATTATTTTCACTGGCGTTTTGATATGTTT
121 ------------+---------+---------+---------+---------+---------+  180
     F  I  E  I  I  F  K  E  G  H  D  Y  F  H  W  R  F  D  M  F
    CCTGGATTCAATAAAAATACTAACGACAGATGGAAtaGCaATATtTTAGAtTTGTTAAGT
181 ------------+---------+---------+---------+---------+---------+  240
     P  G  F  N  K  N  T  N  D  R  W  N  S  N  I  L  D  L  L  S
    CAAAAAGGAAGTTTTTTGTATGAAACTCCAGATGTAATAATTACCAGTTTAAATAATGGA
241 ------------+---------+---------+---------+---------+---------+  300
     Q  K  G  S  F  L  Y  E  T  P  D  V  I  I  T  S  L  N  N  G
    AAAGAAGAAATTTtAATGGcGaTaGAATTTTGTAGTGCTTtACAAGCAGGtaACCAAGCT
301 ------------+---------+---------+---------+---------+---------+  360
     K  E  E  I  L  M  A  I  E  F  C  S  A  L  Q  A  G  N  Q  A
    TGGCAAAGAAGtGGGCGAGCATATTCGGTAggTCGaACAGGGTACCCATATATATACATA
361 ------------+---------+---------+---------+---------+---------+  420
     W  Q  R  S  G  R  A  Y  S  V  G  R  T  G  Y  P  Y  I  Y  I
    GTAGATTTTGTTAAATACGAGTTGAATAATAGTGaTAGATcTAGAAaAAACTTGAGATTC
421 ------------+---------+---------+---------+---------+---------+  480
     V  D  F  V  K  Y  E  L  N  N  S  D  R  S  R  K  N  L  R  F
    CCAAATCCAGcTATACCATATAGTTACATAAGTCACTCAaAAAACACTgGTaATTTTATT
481 ------------+---------+---------+---------+---------+---------+  540
     P  N  P  A  I  P  Y  S  Y  I  S  H  S  K  N  T  G  N  F  I
    GTGCaAGCATATTTTAGAGGAGaAGAATATCAGCCAAAGTATGATAAAAAACTTAAATTT
541 ------------+---------+---------+---------+---------+---------+  600
     V  Q  A  Y  F  R  G  E  E  Y  Q  P  K  Y  D  K  K  L  K  F
    TTTGATGAAACTaTATTTGCAGAaGATGACATTGCAGACTATATAATTGCAAAGCTACAG
601 ------------+---------+---------+---------+---------+---------+  660
     F  D  E  T  I  F  A  E  D  D  I  A  D  Y  I  I  A  K  L  Q
    CATCGCGATACCAGCAATaTAGAACAATTATTGaTAAACAAAaACTTAAAAATGGTTGAA
661 ------------+---------+---------+---------+---------+---------+  720
     H  R  D  T  S  N  I  E  Q  L  L  I  N  K  N  L  K  M  V  E
    TTCtTATCAAAAAATACAAAAaATGATAATAACTTCACATATTCAGaATGGGAGAGTATC
721 ------------+---------+---------+---------+---------+---------+  780
     F  L  S  K  N  T  K  N  D  N  N  F  T  Y  S  E  W  E  S  I
    TACAATGGTACATATAGAATAACAAATTTACCTAGTTTAGGGAGATTTAAATTTAGGAAA
781 ------------+---------+---------+---------+---------+---------+  840
     Y  N  G  T  Y  R  I  T  N  L  P  S  L  G  R  F  K  F  R  K
    AAGATTGCTGAAAAGTCTCTTTCAGGAAAAGTTAAGGAATTTAACAATATTGTTCAGAGA
841 ------------+---------+---------+---------+---------+---------+  900
     K  I  A  E  K  S  L  S  G  K  V  K  E  F  N  N  I  V  Q  R
    TATAGTGTAGGTCTTGCTTCAAGTGATTTACCTTTTGGaGTTATAAGAAAAGAATCAAGA
901 ------------+---------+---------+---------+---------+---------+  960
     Y  S  V  G  L  A  S  S  D  L  P  F  G  V  I  R  K  E  S  R
    AATGaTTTTATTAaCGATGTATGTAAACTTTATAATATAAATGATATGAAAATAATTAAA
961 ------------+---------+---------+---------+---------+---------+  1020
     N  D  F  I  N  D  V  C  K  L  Y  N  I  N  D  M  K  I  I  K
```

FIG. 4B

```
     GAGCTAAAAGAAGATGCGGACCTTATTGTCTGTATGCTTAAGGGATTTAAACCTAGAGGA
1021 ------------+---------+---------+---------+---------+---------+ 1080
      E  L  K  E  D  A  D  L  I  V  C  M  L  K  G  F  K  P  R  G
     GATGATAATCGACCGGATAGAGGAGCGTTACCCCTTGTTGcTATGCTAGCCGGAGAAAAT
1081 ------------+---------+---------+---------+---------+---------+ 1140
      D  D  N  R  P  D  R  G  A  L  P  L  V  A  M  L  A  G  E  N
     GCACAAATTTTTACATTTATTTATGGACCATTAATAAAAGGGGCTATAAATTTGATTGAC
1141 ------------+---------+---------+---------+---------+---------+ 1200
      A  Q  I  F  T  F  I  Y  G  P  L  I  K  G  A  I  N  L  I  D
     CAGGATATCAATAAGCTTGCAAAACGTAACGGGCTTTGGAAATCCTTTGTAAGTTTAAGT
1201 ------------+---------+---------+---------+---------+---------+ 1260
      Q  D  I  N  K  L  A  K  R  N  G  L  W  K  S  F  V  S  L  S
     GACTTTATTGTTTTGGACTGTCCTATTATCGGAGAATCTTATAATGAATTTCGTTTAATC
1261 ------------+---------+---------+---------+---------+---------+ 1320
      D  F  I  V  L  D  C  P  I  I  G  E  S  Y  N  E  F  R  L  I
     ATAAATAAGAACAATAAAGAGTCCATTTTACGCAAAACTAGCAAACAACAAAATATTTTG
1321 ------------+---------+---------+---------+---------+---------+ 1380
      I  N  K  N  N  K  E  S  I  L  R  K  T  S  K  Q  Q  N  I  L
     GTTGATCCAACACCTAATCATTATCAAGAAAATGATGTGGATACAGTTATATACTCTATA
1381 ------------+---------+---------+---------+---------+---------+ 1440
      V  D  P  T  P  N  H  Y  Q  E  N  D  V  D  T  V  I  Y  S  I
     TTTAAATATATTGTACCTAATTGTTTTAGTGGGATGTGTAATCCACCTGGAGGAGACTGG
1441 ------------+---------+---------+---------+---------+---------+ 1500
      F  K  Y  I  V  P  N  C  F  S  G  M  C  N  P  P  G  G  D  W
     AGTGGCCTATCAATAATAAGAAATGGTCATGAATTTAGGTGGTTATCACTTCCTCGAGTT
1501 ------------+---------+---------+---------+---------+---------+ 1560
      S  G  L  S  I  I  R  N  G  H  E  F  R  W  L  S  L  P  R  V
     AGTGAGAATGGAAAAAGACCCGACCATGTAATACAAATACTTGATcTTTTTGAAAAACCC
1561 ------------+---------+---------+---------+---------+---------+ 1620
      S  E  N  G  K  R  P  D  H  V  I  Q  I  L  D  L  F  E  K  P
     CTTTTATTAAGTATTGAGTCAAAAGAAAAACCTAATGATcTTGAACCAAAAATAGGGGTG
1621 ------------+---------+---------+---------+---------+---------+ 1680
      L  L  L  S  I  E  S  K  E  K  P  N  D  L  E  P  K  I  G  V
     CAGTTAATAAAATACATAGAGTATCTATTTGATTTTACTCCTAGTGTTCAAAGAAAGATA
1681 ------------+---------+---------+---------+---------+---------+ 1740
      Q  L  I  K  Y  I  E  Y  L  F  D  F  T  P  S  V  Q  R  K  I
     GCCGGGGGAAATTGGGAGTTTGGTAATAAAAGCCTGGTTCCTAACGATTTTATTCTATTG
1741 ------------+---------+---------+---------+---------+---------+ 1800
      A  G  G  N  W  E  F  G  N  K  S  L  V  P  N  D  F  I  L  L
     TCTGCAGGTGCATTCATCGATTATGACAATCTTACAGAAAATGATTATGAAAAATTTTTT
1801 ------------+---------+---------+---------+---------+---------+ 1860
      S  A  G  A  F  I  D  Y  D  N  L  T  E  N  D  Y  E  K  I  F
     GAAGTCACTGGTTGTGATTTACTGATTGCTATTAAAAACCAGAATAACCCTCAGAAGTGG
1861 ------------+---------+---------+---------+---------+---------+ 1920
      E  V  T  G  C  D  L  L  I  A  I  K  N  Q  N  N  P  Q  K  W
     GTGATTAAATTCAAACCTAAAAATACTATAGCAGAGAAATTAGTTAACTATATAAAGCTT
1921 ------------+---------+---------+---------+---------+---------+ 1980
      V  I  K  F  K  P  K  N  T  I  A  E  K  L  V  N  Y  I  K  L
     AATTTTAAAAGTAATATATTTGATACAGGATTTTTTCATATAGAGGGATAA
1981 ------------+---------+---------+---------+---------+- 2031
      N  F  K  S  N  I  F  D  T  G  F  F  H  I  E  G  *
```

METHOD FOR CLONING AND PRODUCING THE BSMI RESTRICTION ENDONUCLEASE IN *E. COLI*

BACKGROUND OF THE INVENTION

The present invention relates to recombinant DNA which encodes the BsmI restriction endonuclease (endonuclease) as well as two BsmI methyltransferases (methylases, M1 and M2), and expression of BsmI restriction endonuclease from *E. coli* cells containing the recombinant DNA.

BsmI restriction endonuclease is found in the strain of *Bacillus stearothermophilus* NUB36 (New England Biolabs' strain collection #328). It recognizes double-stranded DNA sequence:

5' GAATGCNI↓ 3'
3' CTTACT↑GN 5' (↓/↑ site of cleavage)

and cleaves downstream of its recognition sequence (N1) on the top strand and also cleaves within the recognition sequence on the bottom strand (between G and C of the 5' GCATTC 3' sequence) to generate a 2-base 3' overhanging ends.

Type II and IIs restriction endonucleases are a class of enzymes that occur naturally in bacteria and in some viruses. When they are purified away from other bacterial proteins, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, *Nucl. Acids Res.* 27:312–313, (1999)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTT↓AAA3', 5'PuG↓GNCCPy3' and 5'CACNNN↓GTG3' respectively. *Escherichia coli* RY13, on the other hand, produces only one enzyme, EcoRI, which recognizes the sequence 5'G↓AATTC3'.

A second component of bacterial restriction-modification (R-M) systems are the methyltransferase (methylases). These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. It is only unmodified, and therefore identifiably foreign DNA, that is sensitive to restriction endonuclease recognition and cleavage.

By means of recombinant DNA technology, it is now possible to clone genes and overproduce the enzymes in large quantities. The key to isolating clones of restriction endonuclease genes is to develop a simple and reliable method to identify such clones within complex genomic DNA libraries, i.e. populations of clones derived by 'shot-gun' procedures, when they occur at frequencies as low as $10^{-3}$ to $10^{-4}$. Preferably, the method should be selective, such that the unwanted majority of clones are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophage, cells that carry cloned restriction-modification genes can, in principle, be selectively isolated as survivors from genomic DNA libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985); Tsp45I: Wayne et al. *Gene* 202:83–88, (1997)).

A third approach is to select for active expression of methylase genes (methylase selection) (U.S. Pat. No. 5,200,333 and BsuRI: Kiss et al., *Nucl. Acids. Res.* 13:6403–6421, (1985)). Since R-M genes are often closely linked together, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983);

and MspI: Walder et al., *J. Biol. Chem.* 258:1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535, (1996); Fomenkov et al., *Nucl. Acids Res.* 22:2399–2403, (1994)). This method utilizes the *E. coli* SOS response signals following DNA damages caused by restriction endonucleases or non-specific nucleases. A number of thermostable nuclease genes (TaqI, Tth111I, BsoBI, Tf nuclease) have been cloned by this method (U.S. Pat. No. 5,498,535).

Because purified restriction endonucleases, and to a lesser extent, modification methylases, are useful tools for creating recombinant molecules in the laboratory, there is a commercial incentive to obtain bacterial strains through recombinant DNA techniques that produce large quantities of restriction enzymes. Such overexpression strains should also simplify the task of enzyme purification.

SUMMARY OF THE INVENTION

The present invention relates to a method for cloning the BsmI restriction endonuclease gene from *Bacillus stearo-* thermophilus NUB36. At first the methylase selection method was used to clone the BsmI methylase gene. A methylase positive clone was derived from a plasmid library containing BsmI genomic DNA. However, no apparent BsmI activity was detected in the cell extract of M+ clone.

The DNA insert in the M+ clone was sequenced by primer walking. The clone was found to contain the entire bsmIM1 gene and a small portion (131 bp) of bsmIM2 gene. To the left side of bsmIM1 and bsmIM2 genes, there was one ORF that showed approximately 30% amino acid sequence identity to a DNA partitioning protein (ParA family). Since restriction endonuclease genes are often located adjacent the methylase gene, it was hypothesized that the BsmI endonuclease gene (bsmIR) is probably located to the right side of BsmIM1 and BsmIM2 genes (FIG. 1). Efforts were made to clone the rest of BsmI M2 gene and the entire bsmIR gene by inverse PCR and PCR. After five rounds of inverse PCR and sequencing of the inverse PCR products, the entire sequence of bsmIM2 gene was obtained. An open reading frame (ORF) of 2031 bp was found downstream of BsmI M2 gene and this ORF was named BsmIR gene (FIGS. 1 and 4). Plasmid pBR-BsmIM1 was only partially resistant to BsmI digestion, while pBR-BsmIM2 was fully resistant to BsmI digestion. Both BsmI M1 and M2 genes were amplified by PCR and cloned into vector pBR322 to generate plasmid pBR-BsmIM1&M2. Both BsmI M1 and M2 genes were under the control of $Tc^R$ promoter and expressed constitutively in E. coli. The plasmid pBR-BsmIM1&M2 was fully resistant to BsmI digestion, indicating sufficient expression from the TcR promoter.

The bsmIR gene was amplified by PCR and cloned into a low copy number T7 expression vector pACYC-T7ter with compatible ends. The expression vector pACYC-T7ter is derived from pACYC184 and has 5-8 copies per cell. It contains 4 copies of E. coli transcription terminators upstream of the T7 promoter. The transcription terminators are expected to reduce the run-off transcription from cryptic E. coli promoter(s) on the vector. Cell extracts were prepared and assyed for BsmI endonuclease activity. Two isolates (#11 and #33) dislayed full BsmI activity. The recombinant BsmI yield was determined to be $2 \times 10^6$ units per gram of wet cells (see FIG. 5 for the activity assay). The entire bsmIR gene was sequenced to confirm that #11 carried the wild type bsmIR gene sequence.

Because BsmI endonuclease is a thermostable enzyme, the E. coli cell extract containing BsmI was heated at 65° C. and denatured proteins were removed by centrifugation. The soluable proteins were loaded onto a heparin Sepharose column. The proteins were eluted with a salt gradient of 50 mM to 1 M NaCl. BsmI activity was assayed for each fractions. The most active fractions were also analyzed on an SDS-PAGE (FIG. 6). The observed molecular mass of BsmI endonuclease on the SDS-PAGE is 77.9 kDa, in close agreement with the predicted molecular mass of 78.1 kDa.

BRIEF DESCRIPTION OF THE DRAWINGS

FIG. 2. DNA sequence of BsmI MI methylase gene (SEQ ID NO:1) (bsmIM1) and its encoded amino acid sequence (SEQ ID NO:2).

FIG. 3. DNA sequence of BsmI M2 methylase gene (SEQ ID NO:3) (bsmIM2) and its encoded amino acid sequence (SEQ ID NO:4).

FIG. 4. DNA sequence of BsmI endonuclease gene (SEQ ID NO:5) (bsmIR) and its encoded amino acid sequence (SEQ ID NO:6).

DETAILED DESCRIPTION OF THE INVENTION

The method described herein by which the two BsmI methylase genes and the BsmI restriction endonuclease gene are preferably cloned and expressed in E. coil include the following steps:

1. Construction of BsmI genomic DNA libraries and cloning of bsmIM1 gene.

Genomic DNA is prepared from Bacillus stearothermophilus NUB36 (New England Biolabs collection #328) by the standard procedure. Ten μg genomic DNA is digested with AatII, BspEI, ClaI, HindIII, NdeI, and EcoRI respectively and ligated to a modified pBR322 (2 BsmI sites) with compatible ends. The ligated DNA is transferred into RR1 competent cells by electroporation. More than $10^4$ $Ap^R$ colonies were pooled from the AatII, BspEI, ClaI, HindIII, NdeI, and EcoRI libraries and cells were amplified overnight in 2 liters of LB plus Ap. Plasmid DNA is prepared from the overnight cells. The plasmid libary DNA is digested with BsmI overnight and the challenged DNA is used to transform ER2683 competent cells (McrBC⁻, Mrr⁻, McrA⁻). Surviving transformants were plated at 37° C. overnight on Ap plates. Plasmid mini-preparations were made and digested with BsmI to check if they were resistant to BsmI digestion. Two plasmids (#22 and #54) out of 54 clones were found to be partially resistant to BsmI digestion, indicating that a bsmIM gene had been cloned and expressed in reasonable level in E. coli. No apparent BsmI activity however, was detected in the cell extract of the M+ clone.

Figure 1:
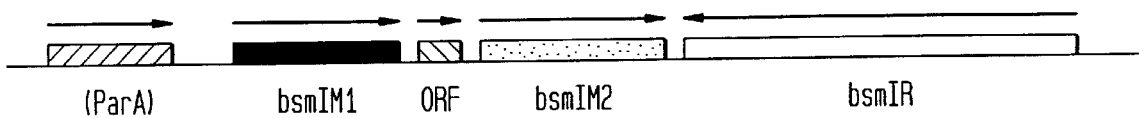
FIG. 1. Gene organization of BsmI restriction-modification system. Genes bsmIM1 and bsmIM2 code for BsmI methylases M1 and M2, respectively. The gene bsmIR codes for BsmI restriction endonuclease. ORF is a small open reading frame between M1 and M2.

The DNA insert in M+ clone #54 was digested with ApoI, NdeI, and PvuII and the DNA fragments were subcloned in pUC19. The inserted fragments were then sequenced using pUC19 universal primer and reverse primer. The rest of the insert was sequenced by primer walking. It was found that the clone ends in an NdeI site and contains the entire bsmIM1 gene and a small portion (131 bp) of bsmIM2 gene. To the left side of bsmIM1 and bsmIM2 genes, there was one ORF that shows 30% amino acid sequence identity to a DNA partitioning protein (ParA family). Since restriction endonuclease genes were usually located adjacent to the methylase gene, it was concluded that BsmI endonuclease gene (bsmIR) was probably located to the right side of bsmIM1 and bsmIM2 genes (FIG. 1). Efforts were made to clone the rest of M2 gene and the entire BsmIR gene by inverse PCR and PCR.

2. Cloning of BsmIM2 and BsmIR genes by inverse PCR and PCR.

Two inverse PCR primers (230–119 and 229–159) were synthesized. BsmI genomic DNA was digested with BsaWI, BspHI, EcoRI, HindIII, MfeI, NlaIII, NspI, SspI, and TaqI, respectively. The digested DNA was purified and self-ligated at a low concentration. The T4 DNA ligase was heat-inactivated and a portion of the ligated DNA was used as the template for inverse PCR. PCR products were found in BsaWI, EcoRI, MfeI, NlaIII, and TaqI templates and gel-purified from a low-melting agarose gel. The purified DNA was sequenced directly using primers 230–119 and 229–159 without the cloning step. This inverse PCR step gave rise to about 540 bp of new DNA sequence in the BsmI M2 gene.

Two inverse PCR primers (232–188 and 232–189) were synthesized. BsmI genomic DNA was digested with BstUI, BstYI, ClaI, DraI, NdeI, RsaI, and XbaI. The digested DNA was purified and self-ligated at a low concentration. The ligase was heat-inactivated and a portion of the ligated DNA was used as the template for inverse PCR. PCR products were found in DraI, and RsaI templates and gel-purified from a low-melting agarose gel. The purified DNA was sequenced directly using primers 232–188 and 232–189 without the cloning step. This inverse PCR step gave rise to about 120 bp of new DNA sequence in the BsmI M2 gene.

Two inverse PCR primers (233–125 and 233–126) were then synthesized. BsmI genomic DNA was digested with BspHI, BstUI, BstYI, ClaI, DraI, EcoRI, HindIII, MfeI, MluI, NdeI, NspI, RsaI, SspI, and XbaI. The digested DNA was purified and self-ligated at a low concentration (2 $\mu$g/ml final). The T4 DNA ligase was heat-inactivated at 65° C. for 30 min and a portion of the ligated DNA was used as the template for inverse PCR. PCR products were found in ClaI, RsaI, SspI, and XbaI templates and gel-purified from a low-melting agarose gel. The purified DNA was sequenced directly using primers 233–125 and 233–126 without the cloning step. Internal primers were also used to sequence the 1600-bp XbaI fragment. This inverse PCR step gave rise to about 1440 bp of new DNA sequence in the BsmI M2 and bsmIR genes.

Two inverse PCR primers (234–167 and 234–168) were synthesized. BsmI genomic DNA was digested with BspHI, BstUI, BstYI, ClaI, DraI, EcoRI, HindIII, MfeI, MluI, NdeI, NspI, RsaI, SspI, and XbaI. The digested DNA was purified and self-ligated at a low concentration. The ligase was heat-inactivated and a portion of the ligated DNA was used as the template for inverse PCR. PCR products were found in HindIII, SspI, and TaqI templates and gel-purified from a low-melting agarose gel. The purified DNA was sequenced directly using primers 234–167 and 234–168 without the cloning step. This inverse PCR step gave rise to about 300 bp of new DNA sequence in the BsmIR genes.

Two inverse PCR primers (238–179 and 238–180) were synthesized. BsmI genomic DNA was digested with ApoI, BglII, DraI, EcoRI, HindIII, KpnI, RsaI, and XbaI. The digested DNA was purified and self-ligated at a low concentration. The ligase was heat-inactivated and a portion of the ligated DNA was used as the template for inverse PCR. PCR products were found in KpnI and RsaI templates and gel-purified from a low-melting agarose gel. The purified DNA was sequenced directly using primers 238–179 and 238–180 without the cloning step. This inverse PCR step gave rise to about 500 bp of new DNA sequence in the bsmIR genes. An ORF of 2031 bp was found downstream of BsmI M2 gene and this ORF was named bsmIR gene (FIGS. 1 and 4).

3. Expression of BsmI M1 and M2 genes in *E. coli*.

Two primers (230–29 and 230–32) were synthesized for PCR amplification of the BsmI Ml gene. The BsmI M1 gene was amplified by PCR using primers 230–29 and 230–32. The PCR product was purified and digested with BamHI and SphI. The PCR DNA again was purified through spin columns and ligated to pBR322 with compatible ends. After transformation into ER2683 competent cells, mini-preparations were performed and the plasmid DNA challenged with BsmI. Twelve isolates were partially resistant to BsmI digestion. It was possible that a second peptide is required for the optimal M1 methylase activity. There was a small ORF of 228 bp (75 amino acid residues) between BsmI Ml and M2 gene. This 75-amino acid peptide may contribute to the optimal M1 activity. Because BsmI M1 may methylate only one strand of the asymmetric BsmI recognition sequence (5' GAATGC 3' or complementary strand 5' GCATTC 3'), a second methylase may be required to methylate the other strand (see M2 expression below).

Two primers (247–322 and 247–323) were synthesized for PCR amplification of the BsmI M2 gene. The BsmI M2 gene was amplified by PCR using primers 247–322 and 247–323. The PCR product was purified and digested with SphI and SalI overnight at 37° C. The PCR DNA again was purified and ligated to pBR322 with compatible ends. Thirteen plasmids were prepared and digested with BsmI. One isolate #9 was shown to be resistant to BsmI digestion. The SphI-SalI fragment containing BsmI M2 gene was gel-purified from a low-melting agarose gel. The purified M2 DNA fragment was ligated to pBR-BsmIM1 with compatible ends. The resulting plasmid was pBR-BsmIM1&M2. Both BsmI M1 and M2 genes are under the control of Tc$^R$ promoter and expressed constitutively in *E. coli*. The plasmid pBR-BsmIM1&M2 is fully resistant to BsmI digestion, indicating sufficient expression from the Tc$^R$ promoter. In accordance with the present invention, it was determined that two methylases were required for full protection of BsmI sites.

4. Expression of BsmI restriction endonuclease (bsmIR) gene in *E. coli*.

Figure 5:
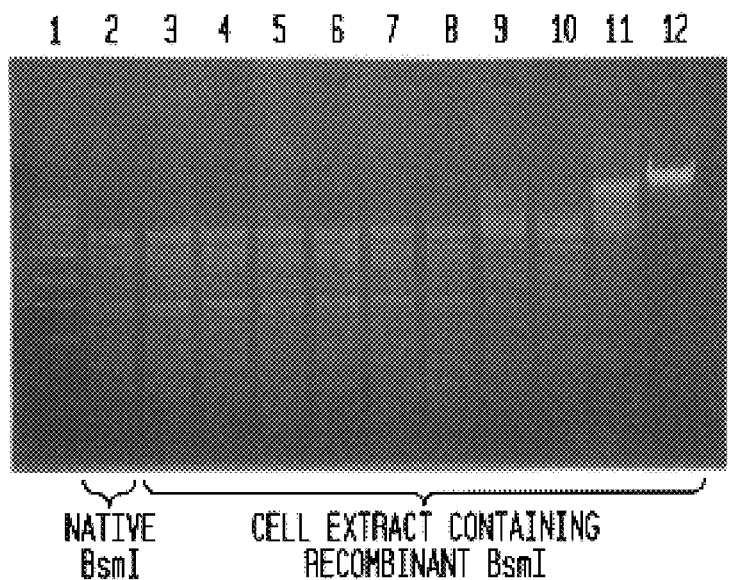
FIG. 5. Recombinant BsmI endonuclease activity in cell extract. Lane 1, 1 kb DNA size marker; lane 2, Lambda DNA cleaved by purified native BsmI; lanes 3 to 12, Lambda DNA cleaved by cell extract containing recombinant BsmI. Dilution factors in lanes 3 to 12 were: 1/100, 1/200, 1/400, 1/800, 1/1600, 1/3200, 1/6400, 1/12800, 1/25600, and 1/51200.

Two primers (241–212 and 235–293) were synthesized for PCR amplification of the bsmIR gene. The bsmIR gene was amplified by PCR using 241–212 and 235–293. The PCR product was purified and digested with NdeI and BamHI overnight at 37° C. The PCR DNA again was purified and ligated to a low copy number T7 expression vector PACYC-T7ter with compatible ends. The expression vector pACYC-T7ter was derived from pACYC184 and has 5–8 copies per cell. It contains 4 copies of *E. coli* transcription terminators upstream of the T7 promoter. The transcription terminators were expected to reduce the run-off transcription from cryptic *E. coli* promoter(s) on the vector. The ligated DNA of bsmIR plus pACYC-T7ter was transformed into BsmI methylase premodified host ER2566 [pBR-BsmIM1&M2]. Thirty-six plasmid mini-preparations were made and six isolates were shown to contain the endonuclease gene insert. Ten ml of cell cultures were made for these six isolates after IPTG induction. Following cell lysis by sonication, the cell extracts were assayed for BsmI endonuclease activity. Two isolates (#11 and #33) dislayed full BsmI activity. Three isolates had partial BsmI activity and one isolate had no activity, probably due to mutation(s) introduced by PCR into the bsmIR gene. The BsmI expression clone #11 was used for 500 ml culture to determine the number of BsmI units per gram of wet cells. The recombinant BsmI yield was determined to be $2\times10^6$ units per gram of wet cells (see FIG. 5 for the activity assay). The entire bsmIR gene was sequenced to confirm that #11 carries the wild type bsmIR gene sequence.

5. Partial purification of BsmI restriction endonuclease

Figure 6:
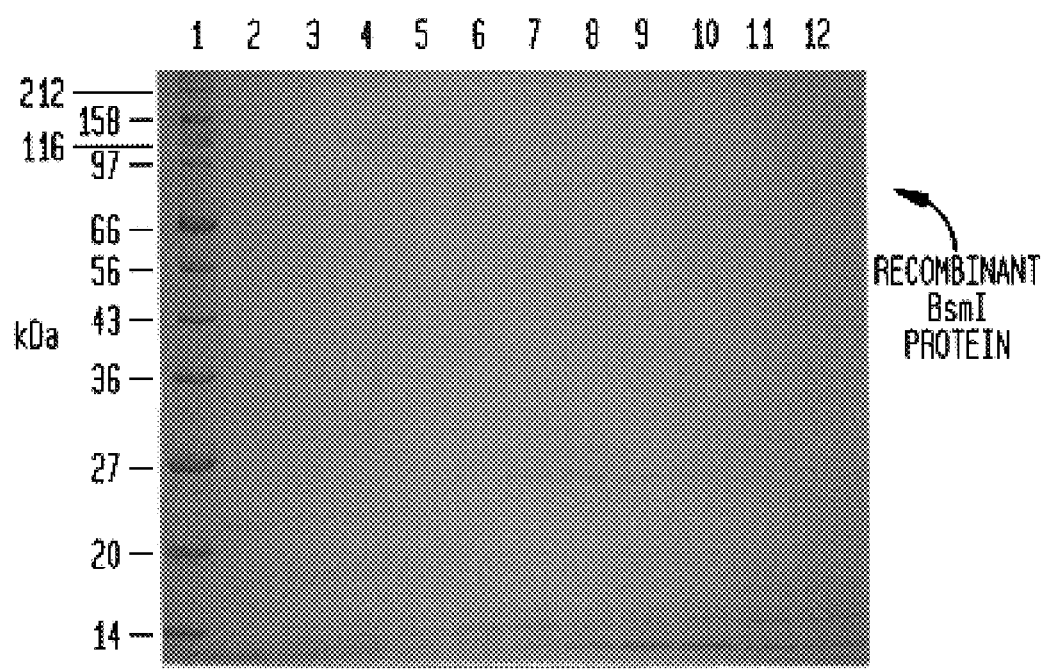
FIG. 6 SDS-PAGE of Partially purified BsmI restriction endonuclease. The predicted molecular mass of BsmI endonuclease is 78.1 kDa. The observed molecular mass on SDS-PAGE is 77.9 kDa. lane 1, protein size marker; lanes 2–12, eluted fractions (19–29) from a heparin Sepharose column.

Because BsmI endonuclease was a thermostable enzyme, *E. coli* cell extract containing BsmI was heated at 65° C. for 30 min and denatured proteins were removed by centrifugation. The soluable proteins were loaded onto a heparin Sepharose column. The column was washed extensively with low salt buffer. The protein was eluted with a salt gradient of 50 mM to 1 M NaCl. BsmI activity was assayed for each fractions. The most active fractions are also analyzed on an SDS-PAGE (FIG. 6). The observed molecular mass of BsmI endonuclease on the SDS-PAGE is 77.9 kDa, in close agreement with the predicted molecular mass of 78.1 kDa.

6. Expression of the long form of BsmI endonuclease

There are two inframe codons (ATG and CAG) upstream of the start codon of bsmIR gene. These two codons encode amino acid residues M (Met) and Q (Gln). The regular BsmI endonuclease is 676-amino acids long. The long form of BsmI endonuclease is 678-amino acids long. To express the long form of BsmI endonuclease, two primers (244–186 and 235–293) are synthesized for PCR amplification of the bsmIR gene (long form). The bsmIR gene (long form) was amplified by PCR using 244–186 and 235–293. The PCR product is purified and digested with NdeI and BamHI overnight at 37° C. The PCR DNA is purified again and ligated to a low copy number T7 expression vector pACYC-T7ter with compatible ends. The ligated DNA of bsmIR (long form) plus pACYC-T7ter was transformed into BsmI methylase premodified host ER2566 [pBR-BsmIM1&M2]. One isolate (#4) was shown to contain the endonuclease gene (long form) insert. Ten ml of cell culture was made for the isolate and induced with IPTG and the cell extract is assayed for BsmI endonuclease activity. #4 cell extract displayed full BsmI activity. It was determined that the long form of BsmI endonuclease with two additional amino acid residues was also active in DNA cleavage.

The present invention is further illustrated by the following Examples. These Examples are provided to aid in the understanding of the invention and are not construed as a limitation thereof.

The references cited above and below are herein incorporated by reference.

EXAMPLE 1

Cloning of BsmI Restriction-modification System in *E.coli*

1. Construction of BsmI genomic DNA libraries and cloning of bsmIM1 gene.

Genomic DNA is prepared from *Bacillus stearothermophilus* NUB36 (New England Biolabs collection #328) by the standard procedure consisting the following steps:

(a) cell lysis by addition of lysozyme (2 mg/ml final), sucrose (1% final), and 50 mM Tris-HCl, pH 8.0;

(b) cell lysis by addition of 10% SDS (final concentration 0.1%);

(c) cell lysis by addition of 1% Triton X-100 and 62 mM EDTA, 50 mM Tris-HCI, pH 8.0;

(d) phenol-$CHCl_3$ extraction of DNA 3 times (equal volume) and $CHCl_3$ extraction one time;

(e) DNA dialysis in 4 liters of TE buffer, change 3×; and (f) RNA was removed by RNase A treatment and the genomic DNA was precipitated in ethanol and resuspended in TE buffer.

Ten µg genomic DNA was digested with AatII, BspEI, ClaI, HindIII, NdeI, and EcoRI respectively for 2 h at 37° C. The vector plasmid pBR322 was also digested with AatII, BspEI, ClaI, HindIII, NdeI, and EcoRI respectively and further treated with CIP for 1 h at 37° C. The vector and genomic DNA samples were purified through Qiagen spin columns. The digested genomic DNA was ligated to pBR322 with compatible ends and incubated at 16° C. onvernight. Following overnight ligation the DNA was dialyzed in 4 L of distilled water on a nitrocellulose membrane by drop dialysis. It was then transferred into RR1 competent cells by electroporation. More than $10^4$ Ap$^R$ colonies were pooled from the AatII, BspEI, ClaI, HindIII, NdeI, and EcoRI libraries and cells were amplified overnight in 2 liters of LB plus Ap. Plasmid DNA was prepared from the overnight cells by Qiagen Maxi-prep columns. 0.2, 0.4, 0.8, 1.6, 3.2 µg of library DNA was digested with BsmI (25 units) overnight and the challenged DNA was used to transform ER2683 competent cells (methylation-dependent restriction minus strain, McrBC$^-$, Mrr$^{-l}$, $^{McrA-}$). Surviving transformants were plated at 37° C. overnight on Ap plates. A total of 54 plasmid mini-preparations were made and digested with BsmI to check if they were resistant to BsmI digestion. Two plasmids (#22 and #54) out of 54 clones were partially resistant to BsmI digestion, indicating that a bsmIM gene had been cloned and expressed in reasonable level in *E. coli*. Ten ml of cells containing #54 plasmid DNA was cultured overnight and cell extract was prepared and used to assay BsmI activity on Lambda DNA. No apparent BsmI activity was detected in cell extract. It was concluded that the bsmIR gene was probably absent in the methylase positive clone (#54) or only a small part of bsmIR gene was present, or the bsmIR gene was not expressed well in *E. coli*. (Later it was demonstrated that no bsmIR gene was present in this M$^+$ clone, see below in the section of cloning and expression of bsmIR gene).

The DNA insert in the M$^+$ clone #54 was digested with ApoI, NdeI, and PvuII and the DNA fragments were subcloned in pUC19. The inserted fragments were then sequenced using pUC19 universal primer and reverse primer. The rest of the insert was sequenced by primer walking. The clone ended in an NdeI site and contains the entire bsmIM1 gene and a small portion (131 bp) of bsmIM2 gene. To the left side of bsmIM1 and bsmIM2 genes, there is one ORF that shows 30% amino acid sequence identity to a DNA partitioning protein (ParA family). Since restriction endonuclease gene is usually located adjacent to the methylase gene, it's concluded that BsmI endonuclease gene (bsmIR) is probably located to the right side of bsmIM1 and bsmIM2 genes (FIG. 1). Efforts were made to clone the rest of M2 gene and the entire bsmIR gene by inverse PCR and PCR.

2. Cloning of bsmIM2 and bsmIR genes by inverse PCR and PCR.

The following inverse PCR primers were synthesized:
5' tatcgtaatattccttgttaattt 3' (230–119) (SEQ ID NO:7)
5' cttaaacgtatagaatctactcag 3' (229–159) (SEQ ID NO:8)

BsmI genomic DNA was digested with BsaWI, BspHI, EcoRI, HindIII, MfeI, NlaIII, NspI, SspI, and TaqI. The digested DNA was purified through Qiagen miniprep spin columns and self-ligated at a low concentration (2 µg/ml final). The ligase was heat-inactivated at 65° C. for 30 min and a portion of the ligated DNA (20–40 ng) was used as the template for inverse PCR. The inverse PCR conditions were 95° C. 1 min, 55° C. 1 min, and 72° C. 1 min for 35 cycles, 5 units of Taq plus Vent® DNA polymerase (50:1 ratio). PCR products were found in BsaWI, EcoRI, MfeI, NlaIII, and TaqI templates and gel-purified from a low-melting agarose gel. The purified DNA was sequenced directly using primers 230–119 and 229–159 without the cloning step.

This inverse PCR step gave rise to about 540 bp of new DNA sequence in the BsmI M2 gene.

The following inverse PCR primers were synthesized:
5' ctagatcctccgtactttaatacg 3' (232–188) (SEQ ID NO:9)
5' aattgtcccatagtatcttccacg 3' (232–189) (SEQ ID NO:10)

BsmI genomic DNA was digested with BstUI, BstYI, ClaI, DraI, NdeI, RsaI, and XbaI. The digested DNA was purified through Qiagen miniprep spin columns and self-ligated at a low concentration (2 μg/ml final). The ligase was heat-inactivated at 65° C. for 30 min and a portion of the ligated DNA (20–40 ng) was used as the template for inverse PCR. The inverse PCR conditions were 95° C. 1 min, 55° C, 1 min, and 72° C. 1 min for 35 cycles. PCR products were found in DraI, and RsaI templates and gel-purified from a low-melting agarose gel. The purified DNA was sequenced directly using primers 232–188 and 232–189 without the cloning step. This inverse PCR step gave rise to about 120 bp of new DNA sequence in the BsmI M2 gene.

The following inverse PCR primers were synthesized:
5' ctttcgatggtaaacgagaagatg 3' (233–125) (SEQ ID NO:11)
5' attttattcctctggagtttagcg 3' (233–126) (SEQ ID NO:12)

BsmI genomic DNA was digested with BspHI, BstUI, BstYI, ClaI, DraI, EcoRI, HindIII, MfeI, MluI, NdeI, NspI, RsaI, SspI, and XbaI. The digested DNA was purified through Qiagen miniprep spin columns and self-ligated at a low concentration (2 μg/ml final). The T4 DNA ligase was heat-inactivated at 65° C. for 30 min and a portion of the ligated DNA (20–40 ng) was used as the template for inverse PCR. The inverse PCR conditions were 95° C. 1 min, 55° C. 1 min, and 72° C. 1 min for 35 cycles, 5 units of Taq plus Vent® DNA polymerase (50:1 ratio). PCR products were found in ClaI, RsaI, SspI, and XbaI templates and gel-purified from a low-melting agarose gel. The purified DNA was sequenced directly using primers 233–125 and 233–126 without the cloning step. Internal primers were also used to sequence the 1600-bp XbaI fragment. This inverse PCR step gave rise to about 1440 bp of new DNA sequence in the BsmI M2 and bsmIR genes.

The following inverse PCR primers were synthesized:
5' atgtgaagttattatcatttttg 3' (234–167) (SEQ ID NO:13)
5' ttcagaatgggagagtatctacaa 3' (234–168) (SEQ ID NO:14)

BsmI genomic DNA was digested with BspHI, BstUI, BstYI, ClaI, DraI, EcoRI, HindIII, MfeI, MluI, NdeI, NspI, RsaI, SspI, and XbaI. The digested DNA was purified through Qiagen miniprep spin columns and self-ligated at a low concentration (2 μg/ml final). The ligase was heat-inactivated at 65° C. for 30 min and a portion of the ligated DNA (20–40 ng) was used as the template for inverse PCR. The inverse PCR conditions were 95° C. 1 min, 55° C. 1 min, and 72° C. 1 min for 35 cycles, 5 units of Taq plus Vent DNA polymerase (50:1 ratio). PCR products were found in HindIII, SspI, and TaqI templates and gel-purified from a low-melting agarose gel. The purified DNA was sequenced directly using primers 234–167 and 234–168 without the cloning step. This inverse PCR step gave rise to about 300 bp of new DNA sequence in the bsmIR genes.

The following inverse PCR primers were synthesized:
5' gaaactccagatgtaataattacc 3' (238–179) (SEQ ID NO:15)
5' tacaaaaaacttccttttgactt 3' (238–180) (SEQ ID NO:16)

BsmI genomic DNA was digested with ApoI, BglII, DraI, EcoRI, HindIII, KpnI, RsaI, and XbaI. The digested DNA was purified through Qiagen miniprep spin columns and self-ligated at a low concentration (2 μg/ml final). The ligase was heat-inactivated at 65° C. for 30 min and a portion of the ligated DNA (20–40 ng) was used as the template for inverse PCR. The inverse PCR conditions were 95° C. 1 min, 55° C. 1 min, and 72° C. 1 min for 35 cycles, 5 units of Taq plus Vent® DNA polymerase (50:1 ratio). PCR products were found in KpnI and RsaI templates and gel-purified from a low-melting agarose gel. The purified DNA was sequenced directly using primers 238–179 and 238–180 without the cloning step. This inverse PCR step gave rise to about 500 bp of new DNA sequence in the bsmIR genes. An ORF of 2031 bp was found downstream of BsmI M2 gene and this ORF was named bsmIR gene (FIGS. 1 and 4).

3. Expression of BsmI M1 and M2 genes in *E. coil*.

Two primers were synthesized for PCR amplification of the BsmI M1 gene.
5' cgcggatccggaggtaaataaatgctttcagaatggattaataccatc 3' (230–29) (SEQ ID NO:17)
5' tatcaagcatgcttataaattcatacaaatttgctcaat 3' (230–32) (SEQ ID NO:18)

The BsmI M1 gene was amplified by PCR using primers 230–29 and 230–32 under condition of 95° C. 30 sec, 55° C 30 sec, and 72° C. 1 min for 25 cycles, 2 units of Vent® DNA polymerase. The PCR product was purified through a Qiagen spin column and digested with BamHI and SphI overnight at 37° C. The PCR DNA again was purified through spin columns and ligated to pBR322 with compatible ends. After transformation into ER2683 competent cells, 36 plasmid mini-preparations were performed and the plasmid DNA challenged with BsmI. Twelve isolates were partially resistant to BsmI digestion. There were a few possible explanations. One explanation was that the the BsmI M1 gene was not efficiently expressed from the $Tc^R$ promoter or the half-life of BsmI M1 protein was very short. The second explanation was that a second peptide was required for the optimal M1 methylase activity. There is a small ORF of 228 bp (75 amino acid residues) between BsmI M1 and M2 gene. This 75-amino acid peptide may contribute to the optimal M1 activity. Because BsmI M1 may methylate only one strand of the asymmetric BsmI recognition sequence (5' GAATGC 3' and 5' GCATTC 3'), a second methylase may be required to methylate the other strand (see M2 expression below).

Two primers were synthesized for PCR amplification of the BsmI M2 gene.
5' tgaagagcatgcggaggtaaataaatgaacaaaatctcttttcaacctgct (247–322) (SEQ ID NO:19)
5' ccctctgtcgactcaccaattaagatataaggattcgaa 3' (247–323) (SEQ ID NO:20)

The BsmI M2 gene was amplified by PCR using primers 247–322 and 247–323 under conditions of 95° C. 30 sec, 55° C. 1.5 min, and 72° C. 2.25 min for 20 cycles, 4 units of Vent® DNA polymerase. The PCR product was purified through a Qiagen spin column and digested with SphI and Sa/I overnight at 37° C. The PCR DNA again was purified through spin columns and ligated to pBR322 with compatible ends. Thirteen plasmids were prepared and digested with BsmI. One isolate #9 was shown to be resistant to BsmI digestion. The SphI-SalI fragment containing BsmI M2 gene was gel-purified from a low-melting agarose gel. The purified M2 DNA fragment was ligated to pBR-BsmIM1 with compatible ends. The resulting plasmid was pBR-BsmIM1&M2. Both BsmI M1 and M2 genes were under the control of $Tc^R$ promoter and expressed constitutively in *E. coli*. The plasmid pBR-BsmIM1&M2 was fully resistant to BsmI digestion, indicating sufficient expression from the $Tc^R$ promoter.

4. Expression of BsmI restriction endonuclease (bsmIR) gene in *E. coil*.

Two primers were synthesized for PCR amplification of the bsmIR gene. The primers had the following sequences:
5' agataaatgcatatgaatgtttttagaattcatggtgataat 3' (241–212) (SEQ ID NO:21)
5' cgcggatccttatccctctatatgaaaaaatcctgt 3' (235–293) (SEQ ID NO:22)

The bsmIR gene was amplified by PCR using 241–212 and 235–293 under conditions of 95° C. 1 min for 1 cycle; 95° C. 45 sec, 55° C. 45 sec, and 72° C. 2 min for 20 cycles, 2 units of Vent® DNA polymerase. The PCR product was purified through a Qiagen spin column and digested with NdeI and BamHI overnight at 37° C. The PCR DNA again was purified through spin columns and ligated to a low copy number T7 expression vector pACYC-T7ter with compatible ends. The expression vector pACYC-T7ter was derived from pACYC184 and had 5–8 copies per cell. It contained 4 copies of E. coli transcription terminators upstream of the T7 promoter. The transcription terminators were expected to reduce the run-off transcription from cryptic E. coli promoter(s) on the vector. The ligated DNA of bsmIR plus pACYC-T7ter was transformed into BsmI methylase pre-modified host ER2566 [pBR-BsmIM1&M2]. Thirty six plasmid mini-preparations were made and six isolates were shown to contain the endonuclease gene insert. Ten ml cell cultures were made for these six isolates and induced with 0.5 mM IPTG for 3 h. Following cell lysis by sonication, the cell debris were removed by centrifugation and the cell extracts were assayed for BsmI endonuclease activity. Two isolates (#11 and #33) displayed full BsmI activity. Three isolates had partial BsmI activity and one isolate had no activity, probably due to mutation(s) introduced by PCR into the bsmIR gene. The BsmI expression clone #11 was used for 500 ml culture to determine the number of BsmI units per gram of wet cells.

Twenty ml of cells ER2566 [pBR-BsmIM1&M2, pACYC-T7ter-BsmIR] were grown overnight at 37° C. in LB plus Ap (100 μg/ml) and Cm (33 μg/ml). The 20 ml overnight cells were inoculated into 500 ml of fresh LB plus Ap (100 μg/ml) and Cm (33 μg/ml). The cells were grown to late log phase for about 3 h and IPTG was added to a final concentration 0.5 mM and induced for 3 h. Cells were harvested and lysed by sonication. Cell debris was removed by centrifugation and cell extract was diluted and assayed for BsmI activity at 65° C. on Lambda DNA for 1 h. The recombinant BsmI yield was determined to be 2×10⁶ units per gram of wet cells (see FIG. 5 for the activity assay). The entire bsmIR gene was sequenced to confirm that #11 carries the wild type bsmIR gene sequence.

The E. coli strain ER2566 [pBR-BsmIM1&M2, pACYC-T7ter-BsmIR] has been deposited under the terms and conditions of the Budapest Treaty with the American Type Culture Collection on Oct. 20, 2000 and received ATCC Accession No. PTA-2614.

5. Partial purification of BsmI restriction endonuclease

Because BsmI endonuclease is a thermostable enzyme, E. coli cell extract containing BsmI was heated at 65° C. for 30 min and denatured proteins were removed by centrifugation. The soluable proteins were loaded onto a heparin Sepharose column. The column was washed extensively with low salt buffer (50 mM NaCl, 10 mM Tris-HCl, pH 7.8, 5 mM β-mercaptoethanol, 1 mM EDTA). The protein was eluted with a salt gradient of 50 mM to 1 M NaCl. The amount of protein was measured in each fractions and BsmI activity was assayed on Lambda DNA. The most active fractions were also analyzed on an SDS-PAGE (FIG. 6). The observed molecular mass of BsmI endonuclease on the SDS-PAGE was 77.9 kDa, in close agreement with the predicted molecular mass of 78.1 kDa.

6. Expression of the long form of BsmI endonuclease

There are two inframe codons (ATG and CAG) upstream of the start codon of bsmIR gene. These two codons encode amino acid residues M (Met) and Q (Gln). The regular BsmI endonuclease is 676-aa long. The long form of BsmI endonuclease is 678-aa long. To express the long form of BsmI endonuclease, two primers were synthesized for PCR amplification of the bsmIR gene (long form).

The primers had the following sequences:
5' agggagagacatatgcagatgaatgtttttagaattcatggt 3' (244–186). (atg and cag are the additional codons) (SEQ ID NO:23)
5' cgcggatccttatccctctatatgaaaaaatcctgt 3' (235–293) (SEQ ID NO:24)

The bsmIR gene (long form) was amplified by PCR using 244–186 and 235–293 under conditions of 95° C. 1 min for 1 cycle; 95° C. 45 sec, 55° C. 45 sec, and 72° C. 2 min for 20 cycles, 2 units of Vent® DNA polymerase. The PCR product was purified through a Qiagen spin column and digested with NdeI and BamHI overnight at 37° C. The PCR DNA again was purified through spin columns and ligated to a low copy number T7 expression vector pACYC-T7ter with compatible ends. The ligated DNA of bsmIR (long form) plus pACYC-T7ter was transformed into BsmI methylase premodified host ER2566 [pBR-BsmIM1&M2]. Eighteen plasmid mini-preparations were made and one isolate (#4) was shown to contain the endonuclease gene (long form) insert. Ten ml of cell culture was made for the isolate and induced with 0.5 mM IPTG for 3 h. Following cell lysis by sonication, the cell debris were removed by centrifugation and the cell extract was assyed for BsmI endonuclease activity. #4 cell extract dislayed full BsmI activity. It was concluded that the long form of BsmI endonuclease with two additional amino acid residues was also active in DNA cleavage.

What is claimed is:

1. Isolated DNA coding for the BsmI restriction endonuclease, wherein the isolated DNA is obtainable from *Bacillus stearothermophilus* NUB36 (New England Biolabs collection #328).

2. A recombinant DNA vector comprising a vector into which a DNA segment encoding the BsmI restriction endonuclease has been inserted.

3. Isolated DNA encoding the BsmI restriction endonuclease and BsmI methylase M1 and M2, wherein the isolated DNA is obtainable from ATCC No. PTA-2614.

4. A cloning vector which comprises the isolated DNA of claim 3.

5. A host cell transformed by the vector of claim 2 or 4.

6. A method of producing recombinant BsmI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO.     : 6,335,190 B1
DATED          : January 1, 2002
INVENTOR(S)    : Jing Zhou, Zhenyu Zhu and Shuang-yong Xu It is certified that error appears in the above-identified patent and that said Letters Patent is hereby corrected as shown below:

Column 1,
Line 22, replace "ends" with -- end --

Column 2,
Line 31, after "359" insert -- , --
Line 42, after "204" insert -- , --

Column 3,
Line 40, replace "dislayed" with -- displayed --
Line 51, replace "fractions" with -- fraction --

Column 7,
Line 6, replace "fractions" with -- fraction --

Column 11,
Line 21, replace "were" with -- was --

Column 12,
Line 10, replace "fractions" with -- fraction --
Line 42, replace "were" with -- was --

Signed and Sealed this

Twenty-first Day of May, 2002

*Attest:*

JAMES E. ROGAN
*Director of the United States Patent and Trademark Office*

*Attesting Officer*

SEQUENCE LISTING

<160> NUMBER OF SEQ ID NOS: 24

<210> SEQ ID NO 1
<211> LENGTH: 828
<212> TYPE: DNA
<213> ORGANISM: Bacillus stearothermophilus
<220> FEATURE:
<221> NAME/KEY: CDS
<222> LOCATION: (1)..(828)

<400> SEQUENCE: 1

```
atg ctt tca gaa tgg att aat acc atc caa aat aca gaa tgt ata caa      48
Met Leu Ser Glu Trp Ile Asn Thr Ile Gln Asn Thr Glu Cys Ile Gln
  1               5                  10                  15
```

```
tca atg aaa aaa tta ccg gat aac tca att gac tta gta att gct gat      96
Ser Met Lys Lys Leu Pro Asp Asn Ser Ile Asp Leu Val Ile Ala Asp
         20                  25                  30 ccc cca tat aat ttg tca aaa gga ggt aaa tgg aaa tgg gat aat agt     144
Pro Pro Tyr Asn Leu Ser Lys Gly Gly Lys Trp Lys Trp Asp Asn Ser
     35                  40                  45 aaa aag ttg gtt ggt atg ggt ggt aat tgg aat aaa gta atg gaa aat     192
Lys Lys Leu Val Gly Met Gly Gly Asn Trp Asn Lys Val Met Glu Asn
 50                  55                  60 tgg gat gat atg aca ttc gaa gag tat tgg gaa ttc acg gag tct tgg     240
Trp Asp Asp Met Thr Phe Glu Glu Tyr Trp Glu Phe Thr Glu Ser Trp
 65                  70                  75                  80 cta ttg gag gta aag cgt att tta aaa cca acg ggt tct cta tgg ata     288
Leu Leu Glu Val Lys Arg Ile Leu Lys Pro Thr Gly Ser Leu Trp Ile
             85                  90                  95 ttt ggt act tat cat aat atg gga ata ata aat gtc gtt tgt cag aag     336
Phe Gly Thr Tyr His Asn Met Gly Ile Ile Asn Val Val Cys Gln Lys
            100                 105                 110 ctt gga ata gaa att ata aat gag att ata tgg tat aag aga aat gca     384
Leu Gly Ile Glu Ile Ile Asn Glu Ile Ile Trp Tyr Lys Arg Asn Ala
        115                 120                 125 ttt cca aat tta tcg ggt cgt aga ttc act gct agt cat gaa aca att     432
Phe Pro Asn Leu Ser Gly Arg Arg Phe Thr Ala Ser His Glu Thr Ile
    130                 135                 140 ctt tgg tgt cat gtt ggc cag aaa aaa agg gaa tat tat ttt aac tat     480
Leu Trp Cys His Val Gly Gln Lys Lys Arg Glu Tyr Tyr Phe Asn Tyr
145                 150                 155                 160 gag tat gtg aaa aat gct tct ttc cct gag gat atg cta aaa tcc cct     528
Glu Tyr Val Lys Asn Ala Ser Phe Pro Glu Asp Met Leu Lys Ser Pro
                165                 170                 175 gga aaa caa atg aga act gtt tgg gat atc cct aat aac aaa caa aaa     576
Gly Lys Gln Met Arg Thr Val Trp Asp Ile Pro Asn Asn Lys Gln Lys
            180                 185                 190 gac gag tta aag ttt gga aaa cat cca act caa aaa cct ctt aga tta     624
Asp Glu Leu Lys Phe Gly Lys His Pro Thr Gln Lys Pro Leu Arg Leu
        195                 200                 205 ctt cat aga ata ata tta gca aca agt aaa gag ggc gat att tgt ctg     672
Leu His Arg Ile Ile Leu Ala Thr Ser Lys Glu Gly Asp Ile Cys Leu
    210                 215                 220 gca ccg ttt agt gga gtt ggt agt gaa tgc gtt gcg gct aag gaa cta     720
Ala Pro Phe Ser Gly Val Gly Ser Glu Cys Val Ala Ala Lys Glu Leu
225                 230                 235                 240 ggg cgg aat ttt ata ggt ttt gaa att aac aag gaa tat tac gat att     768
Gly Arg Asn Phe Ile Gly Phe Glu Ile Asn Lys Glu Tyr Tyr Asp Ile
                245                 250                 255 tct ctt aaa cgt ata gaa tct act cag aaa aaa att gag caa att tgt     816
Ser Leu Lys Arg Ile Glu Ser Thr Gln Lys Lys Ile Glu Gln Ile Cys
            260                 265                 270 atg aat tta taa                                                     828
Met Asn Leu
        275

<210> SEQ ID NO 2
<211> LENGTH: 275
<212> TYPE: PRT
<213> ORGANISM: Bacillus stearothermophilus

<400> SEQUENCE: 2

Met Leu Ser Glu Trp Ile Asn Thr Ile Gln Asn Thr Glu Cys Ile Gln
 1               5                  10                  15
```

```
Ser Met Lys Lys Leu Pro Asp Asn Ser Ile Asp Leu Val Ile Ala Asp
            20                  25                  30

Pro Pro Tyr Asn Leu Ser Lys Gly Gly Lys Trp Lys Trp Asp Asn Ser
        35                  40                  45

Lys Lys Leu Val Gly Met Gly Gly Asn Trp Asn Lys Val Met Glu Asn
    50                  55                  60

Trp Asp Asp Met Thr Phe Glu Glu Tyr Trp Glu Phe Thr Glu Ser Trp
65                  70                  75                  80

Leu Leu Glu Val Lys Arg Ile Leu Lys Pro Thr Gly Ser Leu Trp Ile
                85                  90                  95

Phe Gly Thr Tyr His Asn Met Gly Ile Ile Asn Val Val Cys Gln Lys
            100                 105                 110

Leu Gly Ile Glu Ile Ile Asn Glu Ile Ile Trp Tyr Lys Arg Asn Ala
        115                 120                 125

Phe Pro Asn Leu Ser Gly Arg Arg Phe Thr Ala Ser His Glu Thr Ile
    130                 135                 140

Leu Trp Cys His Val Gly Gln Lys Lys Arg Glu Tyr Tyr Phe Asn Tyr
145                 150                 155                 160

Glu Tyr Val Lys Asn Ala Ser Phe Pro Glu Asp Met Leu Lys Ser Pro
                165                 170                 175

Gly Lys Gln Met Arg Thr Val Trp Asp Ile Pro Asn Asn Lys Gln Lys
            180                 185                 190

Asp Glu Leu Lys Phe Gly Lys His Pro Thr Gln Lys Pro Leu Arg Leu
        195                 200                 205

Leu His Arg Ile Ile Leu Ala Thr Ser Lys Glu Gly Asp Ile Cys Leu
    210                 215                 220

Ala Pro Phe Ser Gly Val Gly Ser Glu Cys Val Ala Ala Lys Glu Leu
225                 230                 235                 240

Gly Arg Asn Phe Ile Gly Phe Glu Ile Asn Lys Glu Tyr Tyr Asp Ile
                245                 250                 255

Ser Leu Lys Arg Ile Glu Ser Thr Gln Lys Lys Ile Glu Gln Ile Cys
            260                 265                 270

Met Asn Leu
        275
```

<210> SEQ ID NO 3
<211> LENGTH: 813
<212> TYPE: DNA
<213> ORGANISM: Bacillus stearothermophilus
<220> FEATURE:
<221> NAME/KEY: CDS
<222> LOCATION: (1)..(813)

<400> SEQUENCE: 3

```
atg aac aaa atc tct ttt caa cct gct ata aaa tgg agt ggc agt aaa    48
Met Asn Lys Ile Ser Phe Gln Pro Ala Ile Lys Trp Ser Gly Ser Lys
 1               5                  10                  15 aga agc caa gca tgg aat ata ata aaa ttg ttt cct aaa ttt gat cga    96
Arg Ser Gln Ala Trp Asn Ile Ile Lys Leu Phe Pro Lys Phe Asp Arg
            20                  25                  30 tat tat gaa ccg ttt gtt ggg ggg gca tcc ata aca tat gct tta aac   144
Tyr Tyr Glu Pro Phe Val Gly Gly Ala Ser Ile Thr Tyr Ala Leu Asn
        35                  40                  45 cca aat aga ggt ata tgc ggt gat ata tgc aaa cca cta att gaa att   192
Pro Asn Arg Gly Ile Cys Gly Asp Ile Cys Lys Pro Leu Ile Glu Ile
    50                  55                  60
```

```
tgg aaa att atc aaa agt gat cct cta agt att gta aat gag tat aaa      240
Trp Lys Ile Ile Lys Ser Asp Pro Leu Ser Ile Val Asn Glu Tyr Lys
 65                  70                  75                  80 aaa aga tgg ata cta ctt caa gag caa gga cat act gta tat tac gaa      288
Lys Arg Trp Ile Leu Leu Gln Glu Gln Gly His Thr Val Tyr Tyr Glu
                 85                  90                  95 att cgc gac aat ttt aac aaa act caa aat ccg tat gac tta ttt ttc      336
Ile Arg Asp Asn Phe Asn Lys Thr Gln Asn Pro Tyr Asp Leu Phe Phe
            100                 105                 110 ctc aca aga act tgt gta aat ggg ctt ata aga ttt aat aaa gat ggt      384
Leu Thr Arg Thr Cys Val Asn Gly Leu Ile Arg Phe Asn Lys Asp Gly
        115                 120                 125 tta ttc aac aat tca ttc cat cat aca aga aaa ggg ata cac cct gat      432
Leu Phe Asn Asn Ser Phe His His Thr Arg Lys Gly Ile His Pro Asp
    130                 135                 140 aag tta cat aaa att atc ttg aat tgg tca tat aga tta aag aat ata      480
Lys Leu His Lys Ile Ile Leu Asn Trp Ser Tyr Arg Leu Lys Asn Ile
145                 150                 155                 160 gaa ttt agg cac ggc gat tat aga gta aca act gaa gat ata aca aaa      528
Glu Phe Arg His Gly Asp Tyr Arg Val Thr Thr Glu Asp Ile Thr Lys
                165                 170                 175 aat gac ttt att tat cta gat cct ccg tac ttt aat acg cgt gga aga      576
Asn Asp Phe Ile Tyr Leu Asp Pro Pro Tyr Phe Asn Thr Arg Gly Arg
            180                 185                 190 tac tat ggg aca att gat ttt aat gaa ttc ctt gaa ttt ctt tat tcg      624
Tyr Tyr Gly Thr Ile Asp Phe Asn Glu Phe Leu Glu Phe Leu Tyr Ser
        195                 200                 205 cta aac tcc aga gga ata aaa ttt gct tta tct ttc gat ggt aaa cga      672
Leu Asn Ser Arg Gly Ile Lys Phe Ala Leu Ser Phe Asp Gly Lys Arg
    210                 215                 220 gaa gat gta aat tac atg gtt gaa tta cca aag gat ttg tat aaa aga      720
Glu Asp Val Asn Tyr Met Val Glu Leu Pro Lys Asp Leu Tyr Lys Arg
225                 230                 235                 240 cat ata tta ata gaa tcc ggt aac tca agt ttc aaa aag gta atg gat      768
His Ile Leu Ile Glu Ser Gly Asn Ser Ser Phe Lys Lys Val Met Asp
                245                 250                 255 aaa gat cct caa aaa gtc ttc gaa tcc tta tat ctt aat tgg tga          813
Lys Asp Pro Gln Lys Val Phe Glu Ser Leu Tyr Leu Asn Trp
            260                 265                 270

<210> SEQ ID NO 4
<211> LENGTH: 270
<212> TYPE: PRT
<213> ORGANISM: Bacillus stearothermophilus

<400> SEQUENCE: 4

Met Asn Lys Ile Ser Phe Gln Pro Ala Ile Lys Trp Ser Gly Ser Lys
 1               5                  10                  15

Arg Ser Gln Ala Trp Asn Ile Ile Lys Leu Phe Pro Lys Phe Asp Arg
                20                  25                  30

Tyr Tyr Glu Pro Phe Val Gly Gly Ala Ser Ile Thr Tyr Ala Leu Asn
            35                  40                  45

Pro Asn Arg Gly Ile Cys Gly Asp Ile Cys Lys Pro Leu Ile Glu Ile
        50                  55                  60

Trp Lys Ile Ile Lys Ser Asp Pro Leu Ser Ile Val Asn Glu Tyr Lys
 65                  70                  75                  80

Lys Arg Trp Ile Leu Leu Gln Glu Gln Gly His Thr Val Tyr Tyr Glu
                 85                  90                  95

Ile Arg Asp Asn Phe Asn Lys Thr Gln Asn Pro Tyr Asp Leu Phe Phe
```

```
            100                 105                 110
Leu Thr Arg Thr Cys Val Asn Gly Leu Ile Arg Phe Asn Lys Asp Gly
        115                 120                 125

Leu Phe Asn Asn Ser Phe His His Thr Arg Lys Gly Ile His Pro Asp
    130                 135                 140

Lys Leu His Lys Ile Ile Leu Asn Trp Ser Tyr Arg Leu Lys Asn Ile
145                 150                 155                 160

Glu Phe Arg His Gly Asp Tyr Arg Val Thr Thr Glu Asp Ile Thr Lys
                165                 170                 175

Asn Asp Phe Ile Tyr Leu Asp Pro Pro Tyr Phe Asn Thr Arg Gly Arg
            180                 185                 190

Tyr Tyr Gly Thr Ile Asp Phe Asn Glu Phe Leu Glu Phe Leu Tyr Ser
        195                 200                 205

Leu Asn Ser Arg Gly Ile Lys Phe Ala Leu Ser Phe Asp Gly Lys Arg
    210                 215                 220

Glu Asp Val Asn Tyr Met Val Glu Leu Pro Lys Asp Leu Tyr Lys Arg
225                 230                 235                 240

His Ile Leu Ile Glu Ser Gly Asn Ser Ser Phe Lys Lys Val Met Asp
                245                 250                 255

Lys Asp Pro Gln Lys Val Phe Glu Ser Leu Tyr Leu Asn Trp
            260                 265                 270

<210> SEQ ID NO 5
<211> LENGTH: 2031
<212> TYPE: DNA
<213> ORGANISM: Bacillus stearothermophilus
<220> FEATURE:
<221> NAME/KEY: CDS
<222> LOCATION: (1)..(2031)

<400> SEQUENCE: 5 atg aat gtt ttt aga att cat ggt gat aat att att gag tgt gag aga       48
Met Asn Val Phe Arg Ile His Gly Asp Asn Ile Ile Glu Cys Glu Arg
  1               5                  10                  15 gtt ata gat ttg ata tta tca aaa atc aat ccc cag aaa gta aaa aga       96
Val Ile Asp Leu Ile Leu Ser Lys Ile Asn Pro Gln Lys Val Lys Arg
             20                  25                  30 ggg ttt att tca tta tca tgc cct ttt ata gaa att ata ttc aaa gag      144
Gly Phe Ile Ser Leu Ser Cys Pro Phe Ile Glu Ile Ile Phe Lys Glu
         35                  40                  45 ggt cat gat tat ttt cac tgg cgt ttt gat atg ttt cct gga ttc aat      192
Gly His Asp Tyr Phe His Trp Arg Phe Asp Met Phe Pro Gly Phe Asn
     50                  55                  60 aaa aat act aac gac aga tgg aat agc aat att tta gat ttg tta agt      240
Lys Asn Thr Asn Asp Arg Trp Asn Ser Asn Ile Leu Asp Leu Leu Ser
 65                  70                  75                  80 caa aaa gga agt ttt ttg tat gaa act cca gat gta ata att acc agt      288
Gln Lys Gly Ser Phe Leu Tyr Glu Thr Pro Asp Val Ile Ile Thr Ser
                 85                  90                  95 tta aat aat gga aaa gaa gaa att tta atg gcg ata gaa ttt tgt agt      336
Leu Asn Asn Gly Lys Glu Glu Ile Leu Met Ala Ile Glu Phe Cys Ser
            100                 105                 110 gct tta caa gca ggt aac caa gct tgg caa aga agt ggg cga gca tat      384
Ala Leu Gln Ala Gly Asn Gln Ala Trp Gln Arg Ser Gly Arg Ala Tyr
        115                 120                 125 tcg gta ggt cga aca ggg tac cca tat ata tac ata gta gat ttt gtt      432
Ser Val Gly Arg Thr Gly Tyr Pro Tyr Ile Tyr Ile Val Asp Phe Val
    130                 135                 140
```

```
                                                          -continued aaa tac gag ttg aat aat agt gat aga tct aga aaa aac ttg aga ttc     480
Lys Tyr Glu Leu Asn Asn Ser Asp Arg Ser Arg Lys Asn Leu Arg Phe
145                 150                 155                 160 cca aat cca gct ata cca tat agt tac ata agt cac tca aaa aac act     528
Pro Asn Pro Ala Ile Pro Tyr Ser Tyr Ile Ser His Ser Lys Asn Thr
                165                 170                 175 ggt aat ttt att gtg caa gca tat ttt aga gga gaa gaa tat cag cca     576
Gly Asn Phe Ile Val Gln Ala Tyr Phe Arg Gly Glu Glu Tyr Gln Pro
        180                 185                 190 aag tat gat aaa aaa ctt aaa ttt ttt gat gaa act ata ttt gca gaa     624
Lys Tyr Asp Lys Lys Leu Lys Phe Phe Asp Glu Thr Ile Phe Ala Glu
    195                 200                 205 gat gac att gca gac tat ata att gca aag cta cag cat cgc gat acc     672
Asp Asp Ile Ala Asp Tyr Ile Ile Ala Lys Leu Gln His Arg Asp Thr
210                 215                 220 agc aat ata gaa caa tta ttg ata aac aaa aac tta aaa atg gtt gaa     720
Ser Asn Ile Glu Gln Leu Leu Ile Asn Lys Asn Leu Lys Met Val Glu
225                 230                 235                 240 ttc tta tca aaa aat aca aaa aat gat aat aac ttc aca tat tca gaa     768
Phe Leu Ser Lys Asn Thr Lys Asn Asp Asn Asn Phe Thr Tyr Ser Glu
                245                 250                 255 tgg gag agt atc tac aat ggt aca tat aga ata aca aat tta cct agt     816
Trp Glu Ser Ile Tyr Asn Gly Thr Tyr Arg Ile Thr Asn Leu Pro Ser
        260                 265                 270 tta ggg aga ttt aaa ttt agg aaa aag att gct gaa aag tct ctt tca     864
Leu Gly Arg Phe Lys Phe Arg Lys Lys Ile Ala Glu Lys Ser Leu Ser
    275                 280                 285 gga aaa gtt aag gaa ttt aac aat att gtt cag aga tat agt gta ggt     912
Gly Lys Val Lys Glu Phe Asn Asn Ile Val Gln Arg Tyr Ser Val Gly
290                 295                 300 ctt gct tca agt gat tta cct ttt gga gtt ata aga aaa gaa tca aga     960
Leu Ala Ser Ser Asp Leu Pro Phe Gly Val Ile Arg Lys Glu Ser Arg
305                 310                 315                 320 aat gat ttt att aac gat gta tgt aaa ctt tat aat ata aat gat atg    1008
Asn Asp Phe Ile Asn Asp Val Cys Lys Leu Tyr Asn Ile Asn Asp Met
                325                 330                 335 aaa ata att aaa gag cta aaa gaa gat gcg gac ctt att gtc tgt atg    1056
Lys Ile Ile Lys Glu Leu Lys Glu Asp Ala Asp Leu Ile Val Cys Met
        340                 345                 350 ctt aag gga ttt aaa cct aga gga gat gat aat cga ccg gat aga gga    1104
Leu Lys Gly Phe Lys Pro Arg Gly Asp Asp Asn Arg Pro Asp Arg Gly
    355                 360                 365 gcg tta ccc ctt gtt gct atg cta gcc gga gaa aat gca caa att ttt    1152
Ala Leu Pro Leu Val Ala Met Leu Ala Gly Glu Asn Ala Gln Ile Phe
370                 375                 380 aca ttt att tat gga cca tta ata aaa ggg gct ata aat ttg att gac    1200
Thr Phe Ile Tyr Gly Pro Leu Ile Lys Gly Ala Ile Asn Leu Ile Asp
385                 390                 395                 400 cag gat atc aat aag ctt gca aaa cgt aac ggg ctt tgg aaa tcc ttt    1248
Gln Asp Ile Asn Lys Leu Ala Lys Arg Asn Gly Leu Trp Lys Ser Phe
                405                 410                 415 gta agt tta agt gac ttt att gtt ttg gac tgt cct att atc gga gaa    1296
Val Ser Leu Ser Asp Phe Ile Val Leu Asp Cys Pro Ile Ile Gly Glu
        420                 425                 430 tct tat aat gaa ttt cgt tta atc ata aat aag aac aat aaa gag tcc    1344
Ser Tyr Asn Glu Phe Arg Leu Ile Ile Asn Lys Asn Asn Lys Glu Ser
    435                 440                 445 att tta cgc aaa act agc aaa caa caa aat att ttg gtt gat cca aca    1392
Ile Leu Arg Lys Thr Ser Lys Gln Gln Asn Ile Leu Val Asp Pro Thr
450                 455                 460
```

```
cct aat cat tat caa gaa aat gat gtg gat aca gtt ata tac tct ata    1440
Pro Asn His Tyr Gln Glu Asn Asp Val Asp Thr Val Ile Tyr Ser Ile
465                 470                 475                 480 ttt aaa tat att gta cct aat tgt ttt agt ggg atg tgt aat cca cct    1488
Phe Lys Tyr Ile Val Pro Asn Cys Phe Ser Gly Met Cys Asn Pro Pro
                485                 490                 495 gga gga gac tgg agt ggc cta tca ata ata aga aat ggt cat gaa ttt    1536
Gly Gly Asp Trp Ser Gly Leu Ser Ile Ile Arg Asn Gly His Glu Phe
            500                 505                 510 agg tgg tta tca ctt cct cga gtt agt gag aat gga aaa aga ccc gac    1584
Arg Trp Leu Ser Leu Pro Arg Val Ser Glu Asn Gly Lys Arg Pro Asp
        515                 520                 525 cat gta ata caa ata ctt gat ctt ttt gaa aaa ccc ctt tta tta agt    1632
His Val Ile Gln Ile Leu Asp Leu Phe Glu Lys Pro Leu Leu Leu Ser
    530                 535                 540 att gag tca aaa gaa aaa cct aat gat ctt gaa cca aaa ata ggg gtg    1680
Ile Glu Ser Lys Glu Lys Pro Asn Asp Leu Glu Pro Lys Ile Gly Val
545                 550                 555                 560 cag tta ata aaa tac ata gag tat cta ttt gat ttt act cct agt gtt    1728
Gln Leu Ile Lys Tyr Ile Glu Tyr Leu Phe Asp Phe Thr Pro Ser Val
                565                 570                 575 caa aga aag ata gcc ggg gga aat tgg gag ttt ggt aat aaa agc ctg    1776
Gln Arg Lys Ile Ala Gly Gly Asn Trp Glu Phe Gly Asn Lys Ser Leu
            580                 585                 590 gtt cct aac gat ttt att cta ttg tct gca ggt gca ttc atc gat tat    1824
Val Pro Asn Asp Phe Ile Leu Leu Ser Ala Gly Ala Phe Ile Asp Tyr
        595                 600                 605 gac aat ctt aca gaa aat gat tat gaa aaa att ttt gaa gtc act ggt    1872
Asp Asn Leu Thr Glu Asn Asp Tyr Glu Lys Ile Phe Glu Val Thr Gly
    610                 615                 620 tgt gat tta ctg att gct att aaa aac cag aat aac cct cag aag tgg    1920
Cys Asp Leu Leu Ile Ala Ile Lys Asn Gln Asn Asn Pro Gln Lys Trp
625                 630                 635                 640 gtg att aaa ttc aaa cct aaa aat act ata gca gag aaa tta gtt aac    1968
Val Ile Lys Phe Lys Pro Lys Asn Thr Ile Ala Glu Lys Leu Val Asn
                645                 650                 655 tat ata aag ctt aat ttt aaa agt aat ata ttt gat aca gga ttt ttt    2016
Tyr Ile Lys Leu Asn Phe Lys Ser Asn Ile Phe Asp Thr Gly Phe Phe
            660                 665                 670 cat ata gag gga taa                                                2031
His Ile Glu Gly
        675

<210> SEQ ID NO 6
<211> LENGTH: 676
<212> TYPE: PRT
<213> ORGANISM: Bacillus stearothermophilus

<400> SEQUENCE: 6

Met Asn Val Phe Arg Ile His Gly Asp Asn Ile Ile Glu Cys Glu Arg
1               5                   10                  15

Val Ile Asp Leu Ile Leu Ser Lys Ile Asn Pro Gln Lys Val Lys Arg
            20                  25                  30

Gly Phe Ile Ser Leu Ser Cys Pro Phe Ile Glu Ile Ile Phe Lys Glu
        35                  40                  45

Gly His Asp Tyr Phe His Trp Arg Asp Met Phe Pro Gly Phe Asn
    50                  55                  60

Lys Asn Thr Asn Asp Arg Trp Asn Ser Asn Ile Leu Asp Leu Leu Ser
65                  70                  75                  80
```

```
Gln Lys Gly Ser Phe Leu Tyr Glu Thr Pro Asp Val Ile Ile Thr Ser
                85                  90                  95
Leu Asn Asn Gly Lys Glu Glu Ile Leu Met Ala Ile Glu Phe Cys Ser
            100                 105                 110
Ala Leu Gln Ala Gly Asn Gln Ala Trp Gln Arg Ser Gly Arg Ala Tyr
        115                 120                 125
Ser Val Gly Arg Thr Gly Tyr Pro Tyr Ile Tyr Ile Val Asp Phe Val
    130                 135                 140
Lys Tyr Glu Leu Asn Asn Ser Asp Arg Ser Arg Lys Asn Leu Arg Phe
145                 150                 155                 160
Pro Asn Pro Ala Ile Pro Tyr Ser Tyr Ile Ser His Ser Lys Asn Thr
                165                 170                 175
Gly Asn Phe Ile Val Gln Ala Tyr Phe Arg Gly Glu Glu Tyr Gln Pro
            180                 185                 190
Lys Tyr Asp Lys Lys Leu Lys Phe Phe Asp Glu Thr Ile Phe Ala Glu
        195                 200                 205
Asp Asp Ile Ala Asp Tyr Ile Ile Ala Lys Leu Gln His Arg Asp Thr
    210                 215                 220
Ser Asn Ile Glu Gln Leu Leu Ile Asn Lys Asn Leu Lys Met Val Glu
225                 230                 235                 240
Phe Leu Ser Lys Asn Thr Lys Asn Asp Asn Asn Phe Thr Tyr Ser Glu
                245                 250                 255
Trp Glu Ser Ile Tyr Asn Gly Thr Tyr Arg Ile Thr Asn Leu Pro Ser
            260                 265                 270
Leu Gly Arg Phe Lys Phe Arg Lys Lys Ile Ala Glu Lys Ser Leu Ser
        275                 280                 285
Gly Lys Val Lys Glu Phe Asn Asn Ile Val Gln Arg Tyr Ser Val Gly
    290                 295                 300
Leu Ala Ser Ser Asp Leu Pro Phe Gly Val Ile Arg Lys Glu Ser Arg
305                 310                 315                 320
Asn Asp Phe Ile Asn Asp Val Cys Lys Leu Tyr Asn Ile Asn Asp Met
                325                 330                 335
Lys Ile Ile Lys Glu Leu Lys Glu Asp Ala Asp Leu Ile Val Cys Met
            340                 345                 350
Leu Lys Gly Phe Lys Pro Arg Gly Asp Asp Asn Arg Pro Asp Arg Gly
        355                 360                 365
Ala Leu Pro Leu Val Ala Met Leu Ala Gly Glu Asn Ala Gln Ile Phe
    370                 375                 380
Thr Phe Ile Tyr Gly Pro Leu Ile Lys Gly Ala Ile Asn Leu Ile Asp
385                 390                 395                 400
Gln Asp Ile Asn Lys Leu Ala Lys Arg Asn Gly Leu Trp Lys Ser Phe
                405                 410                 415
Val Ser Leu Ser Asp Phe Ile Val Leu Asp Cys Pro Ile Ile Gly Glu
            420                 425                 430
Ser Tyr Asn Glu Phe Arg Leu Ile Ile Asn Lys Asn Asn Lys Glu Ser
        435                 440                 445
Ile Leu Arg Lys Thr Ser Lys Gln Gln Asn Ile Leu Val Asp Pro Thr
    450                 455                 460
Pro Asn His Tyr Gln Glu Asn Asp Val Asp Thr Val Ile Tyr Ser Ile
465                 470                 475                 480
Phe Lys Tyr Ile Val Pro Asn Cys Phe Ser Gly Met Cys Asn Pro Pro
                485                 490                 495
```

```
Gly Gly Asp Trp Ser Gly Leu Ser Ile Ile Arg Asn Gly His Glu Phe
            500                 505                 510
Arg Trp Leu Ser Leu Pro Arg Val Ser Glu Asn Gly Lys Arg Pro Asp
        515                 520                 525
His Val Ile Gln Ile Leu Asp Leu Phe Glu Lys Pro Leu Leu Leu Ser
    530                 535                 540
Ile Glu Ser Lys Glu Lys Pro Asn Asp Leu Glu Pro Lys Ile Gly Val
545                 550                 555                 560
Gln Leu Ile Lys Tyr Ile Glu Tyr Leu Phe Asp Phe Thr Pro Ser Val
                565                 570                 575
Gln Arg Lys Ile Ala Gly Gly Asn Trp Glu Phe Gly Asn Lys Ser Leu
            580                 585                 590
Val Pro Asn Asp Phe Ile Leu Leu Ser Ala Gly Ala Phe Ile Asp Tyr
        595                 600                 605
Asp Asn Leu Thr Glu Asn Asp Tyr Glu Lys Ile Phe Glu Val Thr Gly
    610                 615                 620
Cys Asp Leu Leu Ile Ala Ile Lys Asn Gln Asn Asn Pro Gln Lys Trp
625                 630                 635                 640
Val Ile Lys Phe Lys Pro Lys Asn Thr Ile Ala Glu Lys Leu Val Asn
                645                 650                 655
Tyr Ile Lys Leu Asn Phe Lys Ser Asn Ile Phe Asp Thr Gly Phe Phe
            660                 665                 670
His Ile Glu Gly
        675

<210> SEQ ID NO 7
<211> LENGTH: 24
<212> TYPE: DNA
<213> ORGANISM: Synthetic DNA

<400> SEQUENCE: 7
tatcgtaata ttccttgtta attt                                          24

<210> SEQ ID NO 8
<211> LENGTH: 24
<212> TYPE: DNA
<213> ORGANISM: Synthetic DNA

<400> SEQUENCE: 8
cttaaacgta tagaatctac tcag                                          24

<210> SEQ ID NO 9
<211> LENGTH: 24
<212> TYPE: DNA
<213> ORGANISM: Synthetic DNA

<400> SEQUENCE: 9
ctagatcctc cgtactttaa tacg                                          24

<210> SEQ ID NO 10
<211> LENGTH: 24
<212> TYPE: DNA
<213> ORGANISM: Synthetic DNA

<400> SEQUENCE: 10
aattgtccca tagtatcttc cacg                                          24

<210> SEQ ID NO 11
<211> LENGTH: 24
```

```
<212> TYPE: DNA
<213> ORGANISM: Synthetic DNA

<400> SEQUENCE: 11
ctttcgatgg taaacgagaa gatg                                    24

<210> SEQ ID NO 12
<211> LENGTH: 24
<212> TYPE: DNA
<213> ORGANISM: Synthetic DNA

<400> SEQUENCE: 12
attttattcc tctggagttt agcg                                    24

<210> SEQ ID NO 13
<211> LENGTH: 24
<212> TYPE: DNA
<213> ORGANISM: Synthetic DNA

<400> SEQUENCE: 13
atgtgaagtt attatcattt tttg                                    24

<210> SEQ ID NO 14
<211> LENGTH: 24
<212> TYPE: DNA
<213> ORGANISM: Synthetic DNA

<400> SEQUENCE: 14
ttcagaatgg gagagtatct acaa                                    24

<210> SEQ ID NO 15
<211> LENGTH: 24
<212> TYPE: DNA
<213> ORGANISM: Synthetic DNA

<400> SEQUENCE: 15
gaaactccag atgtaataat tacc                                    24

<210> SEQ ID NO 16
<211> LENGTH: 24
<212> TYPE: DNA
<213> ORGANISM: Synthetic DNA

<400> SEQUENCE: 16
tacaaaaaac ttccttttg actt                                     24

<210> SEQ ID NO 17
<211> LENGTH: 48
<212> TYPE: DNA
<213> ORGANISM: Synthetic DNA

<400> SEQUENCE: 17
cgcggatccg gaggtaaata aatgctttca gaatggatta ataccatc          48

<210> SEQ ID NO 18
<211> LENGTH: 39
<212> TYPE: DNA
<213> ORGANISM: Synthetic DNA

<400> SEQUENCE: 18
tatcaagcat gcttataaat tcatacaaat ttgctcaat                    39

<210> SEQ ID NO 19
```

-continued

```
<211> LENGTH: 51
<212> TYPE: DNA
<213> ORGANISM: Synthetic DNA

<400> SEQUENCE: 19
tgaagagcat gcggaggtaa ataaatgaac aaaatctctt ttcaacctgc t            51

<210> SEQ ID NO 20
<211> LENGTH: 39
<212> TYPE: DNA
<213> ORGANISM: Synthetic DNA

<400> SEQUENCE: 20
ccctctgtcg actcaccaat taagatataa ggattcgaa                         39

<210> SEQ ID NO 21
<211> LENGTH: 42
<212> TYPE: DNA
<213> ORGANISM: Synthetic DNA

<400> SEQUENCE: 21
agataaatgc atatgaatgt ttttagaatt catggtgata at                     42

<210> SEQ ID NO 22
<211> LENGTH: 36
<212> TYPE: DNA
<213> ORGANISM: Synthetic DNA

<400> SEQUENCE: 22
cgcggatcct tatccctcta tatgaaaaaa tcctgt                            36

<210> SEQ ID NO 23
<211> LENGTH: 42
<212> TYPE: DNA
<213> ORGANISM: Synthetic DNA

<400> SEQUENCE: 23
agggagagac atatgcagat gaatgttttt agaattcatg gt                     42

<210> SEQ ID NO 24
<211> LENGTH: 36
<212> TYPE: DNA
<213> ORGANISM: Synthetic DNA

<400> SEQUENCE: 24
cgcggatcct tatccctcta tatgaaaaaa tcctgt                            36
```